United States Patent [19]

Sircar

[11] Patent Number: 5,242,939

[45] Date of Patent: Sep. 7, 1993

[54] ANILIDE DERIVATIVES WITH ANGIOTENSIN II ANTAGONIST PROPERTIES

[75] Inventor: Ila Sircar, Ann Arbor, Mich.

[73] Assignee: Warner-Lambert Company, Morris Plains, N.J.

[21] Appl. No.: 757,021

[22] Filed: Sep. 13, 1991

Related U.S. Application Data

[63] Continuation-in-part of Ser. No. 590,626, Sep. 28, 1990, abandoned.

[51] Int. Cl.$^5$ .................. A61K 31/415; A61K 31/44; A61K 31/47; A61K 31/535
[52] U.S. Cl. ................... 524/397; 514/235.2; 514/235.8; 514/307; 514/309; 514/339; 514/341; 514/365; 514/369; 514/381; 514/398; 514/399; 544/132; 544/139; 546/141; 546/142; 546/145; 546/146; 546/273; 546/276; 546/277; 546/278; 548/181; 548/182; 548/183; 548/187
[58] Field of Search ............... 548/336, 337, 342, 343, 548/346, 335, 253, 312.1, 312.7, 313.1, 313.7, 314.7, 315.1, 315.4, 316.4, 322.5, 324.1, 317.1, 317.5, 318.5, 319.5, 181, 182, 183, 187, 189, 204, 253; 514/399, 400, 381, 397, 398, 235.2, 235.8, 302, 309, 339, 341, 365, 369; 546/141, 142, 145, 146, 273, 276, 277, 278; 544/132, 139

[56] References Cited

U.S. PATENT DOCUMENTS 5,041,552  8/1991  Hodges et al. .................. 548/263.8

Primary Examiner—Patricia L. Morris
Attorney, Agent, or Firm—Elizabeth M. Anderson

[57] ABSTRACT

This invention relates to anilide derivatives of Formula I

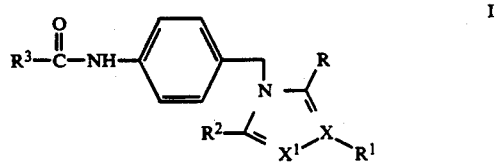

which antagonize the binding of angiotensin II to its receptors. The compounds are useful in the treatment of hypertension, heart failure, glaucoma, and hyperaldosteronism. Methods of making the compounds, novel intermediates useful in the preparation of the compounds, compositions containing the compounds and methods of using them are also covered.

7 Claims, No Drawings

ANILIDE DERIVATIVES WITH ANGIOTENSIN II ANTAGONIST PROPERTIES

CROSS-REFERENCE TO RELATED APPLICATION

This is a continuation-in-part of U.S. Ser. No. 07/590,626, filed Sep. 28, 1990, now abandoned.

BACKGROUND OF THE INVENTION

The instant invention relates to novel anilide derivatives containing substituted imidazole or 1,2,4-triazole moieties which antagonize the binding of angiotensin II (AII) to cellular receptors. This AII antagonist property renders these compounds useful for treatment of angiotensin-related hypertension.

The enzyme renin acts on a blood plasma α-globulin, angiotensinogen, to produce angiotensin I, which is then converted by angiotensin-converting enzyme to AII. The latter substance is a powerful vasopressor agent which has been implicated as a causative agent for producing high blood pressure in various mammals, such as rats, dogs, and humans. The compounds of this invention inhibit the action of AII at its receptors on target cells and thus prevent the increase in blood pressure produced by this hormone-receptor interaction. By administering a compound of the instant invention to a species of mammal with hypertension due to AII, the blood pressure is reduced. The compounds of the invention are also useful for the treatment of congestive heart failure, hyperaldosteronism and glaucoma.

European Application Number 253,310 discloses imidazoles of the formula

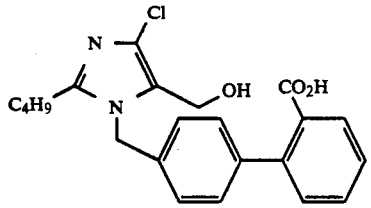

The compounds are disclosed as having utility in treating hypertension and congestive heart failure.

European Application Number 323,841 discloses substituted pyrrole-, pyrazole-, and triazole-containing compounds of the formulas

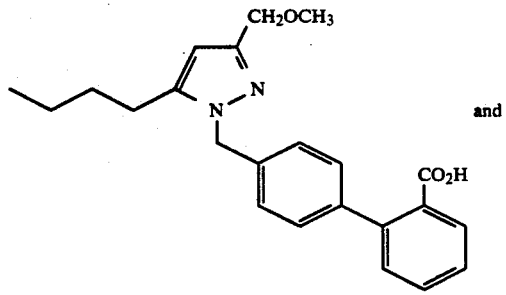

and

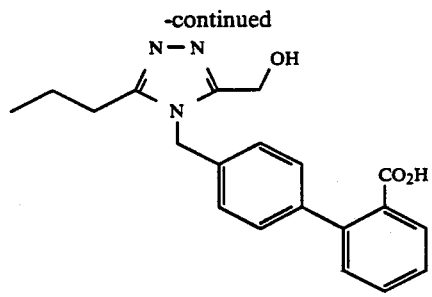

European Application Number 324,377 discloses a pharmaceutical composition of a diuretic or a nonsteroidal antiinflammatory drug useful for blocking the angiotensin II receptor.

U.S. Pat. No. 4,355,040 discloses imidazole-5-acetic acid derivatives of the formula

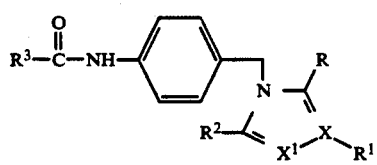

wherein $R^1$ is lower alkyl, cycloalkyl or, phenyl which may be substituted with one to three of halogen, nitro, amino, mono(lower alkyl)amino, di(lower alkyl)amino, lower alkyl, lower alkoxyl, benzyloxyl or/and hydroxyl; $X^1$, $X^2$, and $X^3$ are each hydrogen, halogen, nitro, amino, lower alkyl, lower alkoxyl, benzyloxyl or hydroxyl; Y is halogen and $R^2$ is hydrogen or lower alkyl; provided that $X^1$ is halogen, lower alkyl, lower alkoxyl, benzyloxyl or hydroxyl when $R^1$ is unsubstituted or substituted phenyl only with one halogen, di(lower alkyl)amino, lower alkyl or lower alkoxyl, and its salts. The compounds are disclosed as having antihypertensive activity.

SUMMARY OF THE INVENTION

The instant invention concerns novel anilide derivatives which antagonize the binding of angiotensin II to its receptors. The compounds are those of formula $$R^3-\overset{O}{\underset{\|}{C}}-NH-\underset{}{\text{Ar}}-CH_2-N\underset{R^2}{\overset{R}{\diagup}}\underset{X^1}{\diagdown}\underset{R^1}{\diagdown} \quad I$$

or the pharmaceutically acceptable acid addition or basic salts thereof wherein X, $X^1$, R, $R^1$, $R^2$, and $R^3$ are as defined below.

The invention also includes a pharmaceutical composition comprising an antihypertensive effective amount of a compound of Formula I above in admixture with a pharmaceutically acceptable carrier or excipient and a method for treating renin-associated hypertension in a mammal suffering therefrom which comprises administering to said mammal the above pharmaceutical composition in unit dosage form.

Further the invention includes a pharmaceutical composition comprising an amount of a compound of Formula I above effective for treating renin-associated hyperaldosteronism in admixture with a pharmaceutically acceptable carrier or excipient, and a method for treating hyperaldosteronism in a mammal suffering therefrom comprising administering to said patient the above pharmaceutical composition in unit dosage form.

Also the invention includes a pharmaceutical composition comprising an amount effective for treating congestive heart failure of a compound of Formula I above in admixture with a pharmaceutically acceptable carrier or excipient and a method of treating congestive heart failure in a patient suffering therefrom comprising administering to said patient the above pharmaceutical composition in unit dosage form.

Also the invention includes a pharmaceutical composition comprising an amount of a compound of Formula I above effective for treating glaucoma in admixture with a pharmaceutically acceptable carrier or excipient; and a method of treating glaucoma in a patient suffering therefrom comprising administering to said patient the above pharmaceutical composition in unit dosage form.

The instant invention further includes methods for making compounds of Formula I.

DETAILED DESCRIPTION

The following table provides a dictionary of the terms used in the description of the invention.

TABLE I

| Abbreviation | |
|---|---|
| | Protecting Group |
| BOC | Tert-Butyloxycarbonyl |
| CBZ | Benzyloxycarbonyl |
| Bn | Benzyl |
| Ac | Acetyl |
| | Solvents |
| MeOH | Methanol |
| DMF | N,N-Dimethyl formamide |
| THF | Tetrahydrofuran |
| EtOAc | Ethyl acetate |
| | Reagents |
| DCC | N,N'-Dicyclohexyl carbodiimide |
| HOBT | 1-Hydroxybenzotriazole |
| TFA | Trifluoroacetic acid |

The compounds of the present invention are represented by the formula

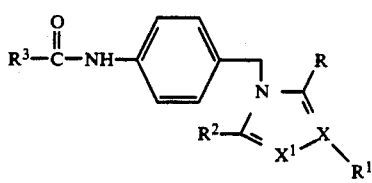

I or the pharmaceutically acceptable acid addition of base salts thereof, wherein:
X and $X^1$ are each independently carbon or nitrogen;
R and $R^1$ are each independently
  hydrogen,
  halogen,
  lower alkyl,
  alkyl carboxylate,
  alkyl carboxylic acid,
  trihalomethyl,
  perfluoroethyl,
  acetyl ester,
  cyano,
  cyanomethyl,
  acetamide,
  alkoxymethyl,
  hydroxymethyl,
  alkylthiomethyl,
  thiomethyl,
  $CO_2H$
  $(CH=CH)-CO_2R_8$ wherein $R_8$ is H or lower alkyl,
  $CO_2$alkyl,
  CHO,
  1-oxoalkyl,
  2-oxoalkyl, or
  3-oxoalkyl
with the proviso that when X is nitrogen, $R^1$ is absent,
when X is carbon, R and $R^1$ together form a 5- or 6-membered aromatic ring which ring may contain one or more heteroatoms selected from N, S, O and ring may be unsubstituted or substituted with halo, alkyl, alkyloxy, alkylthio, alkylcarboxy, $CO_2H$, $NO_2$, $NH_2$, or dialkylamine,
when X is carbon, R and $R^1$ are each independently vinyl; cycloalkylidenyl; alkynyl of 2 to 10 carbon atoms; phenylalkynyl where the alkynyl portion is 2 to 6 carbon atoms, aryl, heteroaryl, containing one or more heteroatoms selected from N, O, and S; N-pyrrolyl, N-1,2,4-triazolyl, N-1,3,4-triazolyl, N-pyrazolyl, N-imidazolyl which heteroaryl is unsubstituted or substituted by a moiety selected from halogen, alkyl, alkyloxy, alkylthio, alkylcarboxy, $CO_2H$, $NO_2$, $NH_2$, and dialkylamino;
$R^2$ is
  propyl,
  butyl,
  cycloalkyl
  $-CH_2CH=CH_2$,
  $-CH=CHCH_3$,
  $-CH_2CH=CH-CH_3$,
  $-CH=CHCH_2CH_3$,
  $-CH_2CH_2CH=CH_2$,
  $-CH_2C\equiv CH$,
  $-C\equiv C-CH_3$,
  $-C\equiv C-CH_2CH_3$,
  $-CH_2C\equiv CCH_3$,
  $-CH_2CH_2C\equiv CH$,
  $-SCH_3$,
  $-SC_2H_5$,
  $-SC_3H_7$,
  $-SC_4H_9$,
  $-OCH_3$,
  $-OC_2H_5$,
  $-OC_3H_7$,
  $-OC_4H_9$,
  $-SCH_2CH=CH_2$,
  $-OCH_2CH=CH_2$,
  $-SCH_2C\equiv CH$, or
  $-OCH_2C\equiv CH$; and
$R_3$ is

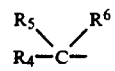

wherein

R₄ is hydrogen, lower alkyl, aryl, unsubstituted or substituted with halo, alkyl, alkyloxy, hydroxy, arylalkyl, unsubstituted or substituted with halo, alkyl, alkyloxy, hydroxy, heteroaryl, unsubstituted or substituted with halo, alkyl, alkyloxy, hydroxy, or heteroarylalkyl, unsubstituted or substituted with halo, alkyl, alkyloxy, hydroxy; when R₅ is hydrogen, R₆ is —C≡N, —COOH, tetrazole, or

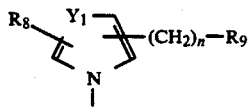

wherein
Y₁ is CH or N,
n is from 0 to 2,
R₉ is
  H,
  lower alkyl
  aryl,
  CN,
  COR₈,
  —CO₂R₈,

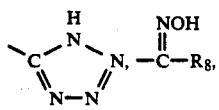

wherein R₈ is hydrogen or lower alkyl; when Y₁ is CH, Y₁ and R₈ together may form

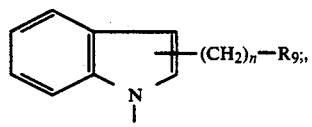

and R₅ and R₆ when taken together are

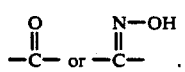

More preferred compounds of the instant invention are those compounds of Formula I wherein
X and X¹ are each independently carbon or nitrogen;
R and R¹ are each independently,
—CH₂OH,
—CH₂SH,
—CH₂OCH₃,
—CH₂SCH₃,
—CHO

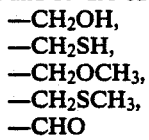

—CH₃,
—CF₂₃,
—CH₃,
—H,
—Cl,
—Br,
—F,
CH=CHCO₂R₈
—(CH₂)ₙCO₂R₈, wherein R₈ is H or lower alkyl;
—(CH₂)ₙC≡N,
—(CH₂)ₙCONH₂,
—(CH₂)ₙCONHCH₃, or
—(CH₂)ₙCON(CH₃)₂
wherein n is 0, 1, or 2; with the proviso that when X is nitrogen, R¹ is absent;
R² is
  propyl,
  butyl,
  cyclopropyl
  thiomethyl,
  thioethyl,
  thiopropyl,
  thiobutyl,
  —CH₂CH=CH₂,
  —CH₂CH=CH=CH₃,
  —CH₂CH₂CH=CH₂,
  —CH₂C≡CCH₃,
  —CH₂CH₂C≡CH,
  —OCH₃,
  —OCH₂H₅,
  —OC₃H₇,
  —OC₄H₉,
  —SCH₂CH=CH₂ or
  —OCH₂CH=CH₂; and
R₃ is as above.

Most preferred compounds of the invention are those wherein
R is (CH₂)ₙCO₂H; wherein n is an integer of from 0 to 2
X is carbon;
X¹ is nitrogen;
R¹ is Cl or Br;
R₂ is butyl or propyl;
R₃ is

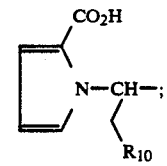

and
R₁₀ is phenyl or thienyl.

Most especially preferred compounds of the present invention are selected from the list consisting of:
(S) 1H-pyrrole-2 carboxylic acid, 1-[2-[[4-[[2-butyl-4-chloro-5-(hydroxymethyl) -1H imidazol-1-yl]-methyl]phenyl]amino]-2 oxo-1-(phenylmethyl)ethyl]-methyl ester;

(S) 1H-pyrrole-2-carboxylic acid, 1-[2-[[4-[[2-butyl-4-chloro-5-(hydroxymethyl) -1H-imidazol-1-yl]-methyl]phenyl]amino]-2-oxo 1-(phenylmethyl)ethyl];

N-[4-[[2-butyl-4-chloro-5-(hydroxymethyl)-1H-imidazol-1-yl]methyl]phenyl]-α-oxo-benzeneacetamide;

N [4-[[2-butyl-4-chloro-5-(hydroxymethyl)-1H-imidazol-1-yl]methyl]phenyl]-γ-(hydroxyimino)benzeneacetamide;

(S) 1H-pyrrole-2-carboxylic acid, 1-[2-[[4-[[3-(hydroxymethyl)-5-(propylthio)-4H-1,2,4-triazol-4-yl]methyl]phenyl]amino]-2-oxo-1-(phenylmethyl)ethyl]-methyl ester;

N-[4-[[2-butyl-4-chloro-5-(hydroxymethyl)-1H-imidazol-1-yl]methyl]phenyl]-α-cyano-benzenepropanamide;

(S) 1H-pyrrole-2-carboxylic acid, 1-[2-[[4-[[2-butyl-4-chloro-5-(hydroxymethyl)-1H-imidazol-1-yl]methyl]phenyl]amino]-2-oxo-1-phenylethyl] methyl ester;

(S) 1H-pyrrole-2-carboxylic acid, 1-[2-[[4-[[2-butyl-4-chloro-5-(hydroxymethyl)-1H-imidazol-1-yl]methyl]phenyl]amino]-1-butyl-2-oxoethyl] methyl ester;

(S) 1H pyrrole-2-carboxylic acid, 1-[2-[[4-[[2-butyl-4-chloro-5-(hydroxymethyl)-1H-imidazol-1-yl]methyl]phenyl]amino]-2-oxoethyl] methyl ester;

(S) Methyl 2-butyl-5 chloro-3-[[4-[[2-[2-(methoxycarbonyl)-1H-pyrrol-1-yl]-1-oxo-3-(2-thienyl)propyl]amino]phenyl]methyl]-3H-imidazole-4-acetate;

(S) Methyl 2-butyl-5-chloro-3-[[4-[[2-[2-(methoxycarbonyl)-1H-pyrrol-1-yl]-1-oxo-3-phenylpropyl]amino]phenyl]methyl]-3H-imidazole 4-acetate;

(S) Methyl 2-butyl-5-chloro-3-[[4-[[2-[[3-(ethoxycarbonyl)-2-methyl]-1H-pyrrol-1-yl]-1-oxo-3-phenylpropyl] amino]phenyl]methyl]-3H-imidazole-4-acetate;

(S) Methyl 1-[2-[[4-[(2-butyl 4-methylimidazol-1-yl)methyl]phenyl]amino]-2-oxo-1-(phenylmethyl)ethyl]-1H-pyrrole 2-carboxylate;

(S) Methyl 2-butyl-5-chloro-3-[[4-[[2-[2(methoxycarbonyl)-1H-pyrrol-1-yl]-1-oxo-3-phenylpropyl]amino]phenyl]methyl]-3H-imidazole-4-propanoate;

(S) Methyl 1-[2-[4-[2-ethyl-5,7-dimethyl-3H-imidazo[4,5-b]pyridin-3-yl)methyl]phenyl]amino]-2-oxo 1-(phenylmethyl)ethyl]-1-pyrrole-2-carboxylate;

(S) 1H-Pyrrole-2-carboxylic acid, 1-[2-[[4-[[2-butyl-4-chloro-5-(hydroxymethyl)-1H-imidazol-1 yl]methyl]phenyl]amino]-2-oxo-1-(phenylmethyl)ethyl];

(S) 2-Butyl-3-[[4-[[-2-(-2-carboxy-1H pyrrol-1-yl)-1-oxo-3-phenylpropyl]amino]phenyl]methyl]-5-chloro-3H-imidazole-4-acetic acid;

(S) 2-Butyl-3-[[4-[[2-(-2-carboxy-1H-pyrrol-1-yl)-1-oxo 3-(2-thienyl) propyl]amino]phenyl]methyl]-5-chloro-3H-imidazole 4-acetic acid;

(S) 2-Butyl-3-[[4-[[2-(3-ethoxycarbonyl-2-methyl-1H-pyrrol-1-yl) -1-oxo-3-phenylpropyl]amino]phenyl]methyl]-5-chloro-3H-imidazole-4-acetic acid;

(S) 2-Butyl-5-chloro-3-[[4-[[2-[2-(methoxycarbonyl)-1H-pyrrol-1-yl]-1-oxo-3-phenylpropyl]amino]-phenyl]methyl]-3H-imidazole-4-propanoic acid;

(S) 1-[2-[[4-[(2-Butyl-4-methyl-1H-benzimidazole-1-yl)methyl]phenyl]amino]-2-oxo-1-(phenylmethyl)ethyl]-1H-pyrrole-2-carboxylic acid;

(S) 1-[2-[[4-[(5,7-dimethyl-2-ethyl-3Himidazo[4,5-b]pyridin-3-yl)methyl]phenyl]amino-2-oxo-(phenylmethyl)ethyl]-1H-pyrrole-2-carboxylic acid;

(S) 1-4-chloro-1-[[4-[[2-[2-(methoxycarbonyl)-1H -pyrrol-1-yl]-1-oxo-3-phenylpropyl]amino]phenyl]methyl]-1H-imidazole-5-carboxylate;

(S) 2-Butyl-1-[[4-[[2-(2-carboxy-1H-pyrrol-1-yl)-1-oxo-3-phenylpropyl]amino]phenyl]methyl]-4-chloro-1H-imidazole-5-carboxylic acid;

and their pharmaceutically acceptable salts.

The compounds of the instant invention include solvates, hydrates, and pharmaceutically acceptable acid addition salts of the basic compounds of Formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared, when applicable, by contacting the free base form with a sufficient amount of the desired acid to produce a salt in the conventional manner. The free base forms may be regenerated by treating the salt form with a base.

When the compounds are in the free carboxylic acid form the pharmaceutically suitable salts also include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity, and solubility. Preferred salts of this invention for the reasons cited above include potassium, sodium, calcium, and ammonium salts.

The compounds of the present invention possess one or more chiral centers and each center may exist in the R(D) or S(L) configuration. The present invention includes all enantiomeric and epimeric as well as the appropriate mixtures thereof.

The instant invention includes a process for the preparation of triazolo-containing compounds of Formula I which comprises:

a) reacting 4-nitrobenzylamine with di-2-pyridyl-thiocarbonate to produce the corresponding isothiocyanate, b) adding an acid hydrazide to the isothiocyanate to produce the corresponding thiosemicarbazide, c) cyclizing using an aqueous inorganic base and heat and then acidification to produce the corresponding triazole-thione, d) alkylating the product of Step c) with an alkylhalide in the presence of an organic base in a polar solvent and subsequent hydrogenation to produce an aminobenzyltriazole, e) acylating with the requisite acid to produce a compound of Formula I, which may be converted if desired to a pharmaceutically acceptable salt thereof.

The instant invention also includes a process for the preparation of imidazole containing compounds of Formula I which comprises:

a) reducing and acylating

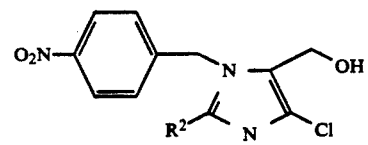

wherein $R^2$ is as defined above with a desired amino acid derivative and b) deprotecting the product of Step a) to produce a desired compound of Formula I which may, if desired, be converted to a corresponding pharmaceutically acceptable salt thereof.

The instant invention also includes a process for the preparation of an imidazole containing compound according to claim 1 which comprises:

a) reducing and acylating

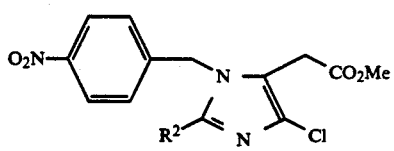

b) deprotecting the product of Step a) to produce a desired compound of Formula I which may, if desired, be converted to a corresponding pharmaceutically acceptable salt thereof.

The term protecting group refers to those groups intended to protect against undesirable reactions during synthetic procedures includes but is not limited to BOC, CBZ, Bn, and Ac.

The term lower alkyl refers to straight or branched chain alkyl radicals containing from one to six carbon atoms including but not limited to methyl, ethyl, n-propyl, isopropyl, n-butyl, iso-butyl, secbutyl, 2-methylhexyl, n-pentyl, 1-methylbutyl, 2,2-dimethylbutyl, 2-methyl-pentyl, 2,2-dimethylpropyl, n-hexyl, and the like.

The term halogen refers to bromine, chlorine, and fluorine.

The term alkyl carboxylate refers to groups —$CO_2$alkyl wherein alkyl is as above; the preferred alkyls are methyl and ethyl.

The term trihalomethyl refers to the halogens as above; the preferred group is trifluoromethyl.

The term acetyl ester refers to groups —$CH_2CO_2$alkyl wherein alkyl is as described above; the preferred groups are $CH_2CO_2CH_3$ and $CH_2CO_2C_2H_5$.

The term acetamide refers to groups —$CH_2CON(R)_2$ wherein the R substituents can each independently be hydrogen or lower alkyl; the preferred acetamides are —$CH_2CONH_2$, —$CH_2CONHCH_3$, and —$CH_2CON(CH_3)_2$.

The term alkoxymethyl refers to groups —$CH_2OR$ wherein the R substituent is lower alkyl as above; the preferred groups are —$CH_2OCH_3$ and —$CH_2OC_2H_5$.

The term alkylthiomethyl refers to groups wherein alkyl is as defined above; the preferred group is —$CH_2SCH_3$.

The terms 1-oxoalkyl, 2-oxoalkyl, and 3-oxoalkyl refer to groups wherein alkyl is as defined above; preferred are

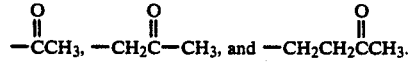

The term Ar or aryl refers to phenyl and 1- or 2-naphthyl, unsubstituted or substituted by $CH_3$, $OCH_3$, OH, Br, Cl, F, $NO_2$, $NH_2$, $N(CH_3)_2$, $SCH_3$, SH.

Alkyl, when used in the term aralkyl, is as described above.

Heteroaryl refers to 5- or 6 membered rings or 8-, 9-, or 10-membered twin rings containing one or more heteroatoms selected from N, O, S, and includes but is not limited to: pyrrole, imidazole, thiophene, furan, pyridine, thiazole, indole, morpholine is another 6-memberd ring formed by $R^1$ and $R^2$ taken together, isoquinoline.

Alkyl, when used in the term heteroalkyl, is as described above.

The syntheses of compounds of the Formula I are exemplified in Schemes I and II below. The first route begins with 4-nitrobenzylamine (2 which is converted in situ to its isothiocyanate by reacting with thiophosgene and an organic base such as triethylamine or by reacting with a thiophosgene equivalent such as di-2-pyridyl-thiocarbonate or thiocarbonyldiimidazole in an inert solvent such as dichloromethane, ether, tetrahydrofuran, or chloroform. Subsequent addition of an acid hydrazide such as glyoxylic acid hydrazide affords the thiosemicarbazide, 3. Cyclization occurs upon brief heating with an aqueous inorganic base such as KOH, NaOH, $K_2CO_3$, or $Na_2CO_3$. Acidification on work-up affords the triazole-thione, 4.

Alkylation at sulfur occurs by treatment with an alkyl halide such as ethyl iodide, propyl iodide, allyl bromide, or 1 bromo-2 butene in the presence of an organic base such as diisopropylethyl-amine or triethylamine in a polar solvent such as DMF or DMA. Subsequent hydrogenation over Raney nickel catalyst affords the aminobenzyl-triazole, 5. Acylation affords compound which is an example of compounds of the Formula I.

Scheme II shows a second route that employs 9, which is prepared in a manner analogous to that of Furakawa, et al, U.S. Pat. No. 4,355,040, Example 17, as the starting material. Similar to Scheme I, Compound 9 may be reduced and acylated to afford compounds 10 and 12 which are examples of a compound of Formula I. Subsequent saponification or oximination reactions afford compounds 11 and 13 which are also examples of a compound of Formula I.

Similar to Scheme II, Scheme III shows a third route that employs compound 14. Compound 14 may be reduced and acylated to afford compound 15 which upon saponification affords compound 16. Both compounds 15 and 16 are examples of a compound of Formula I.

Scheme I

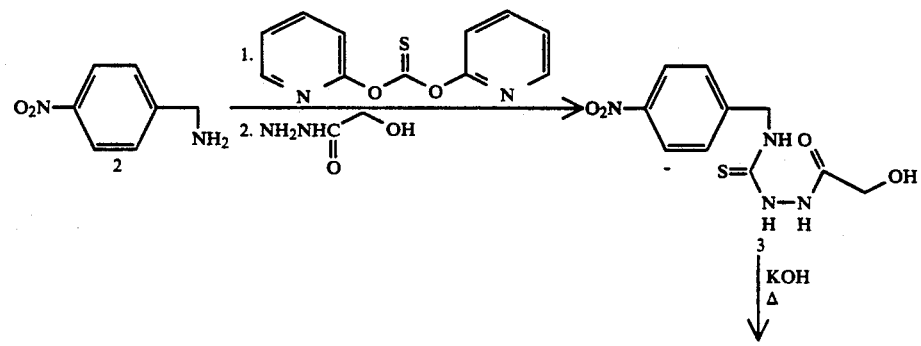

-continued
Scheme I
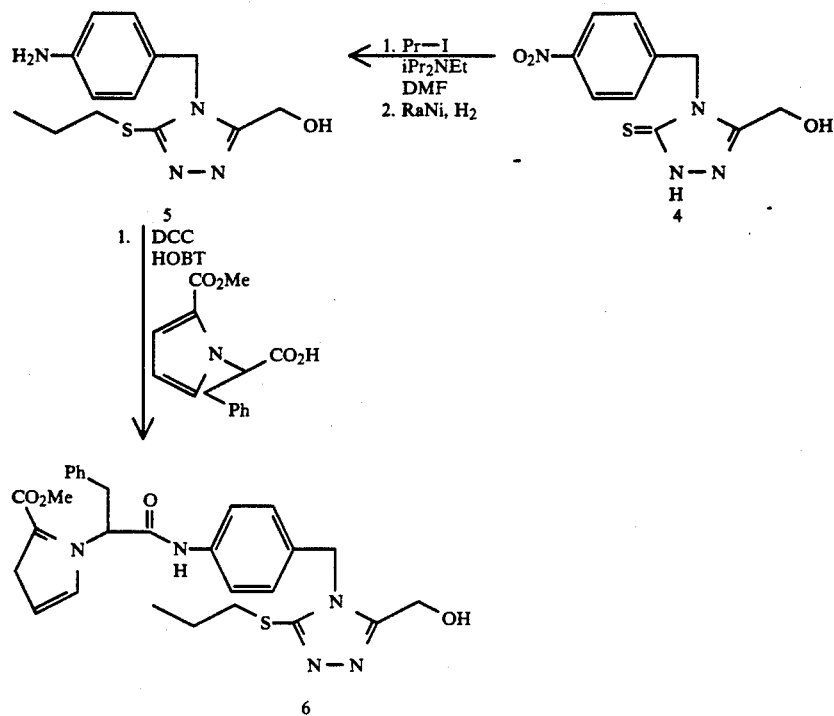
Scheme II
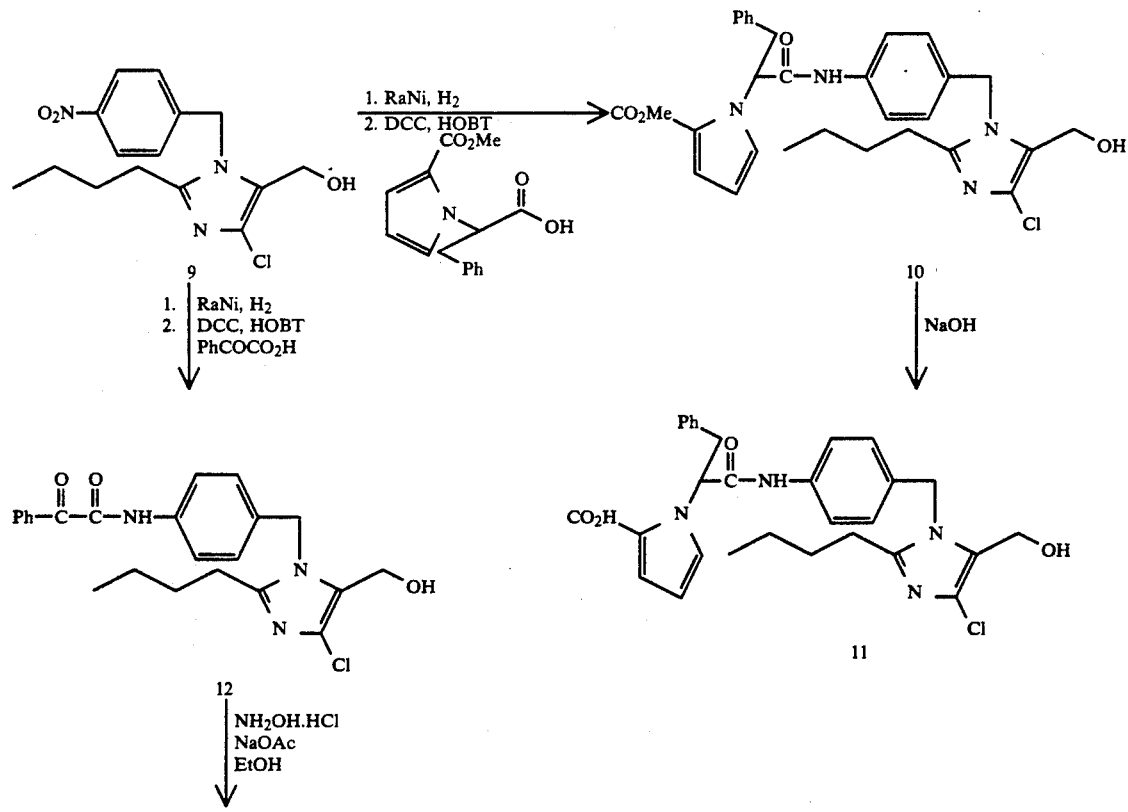

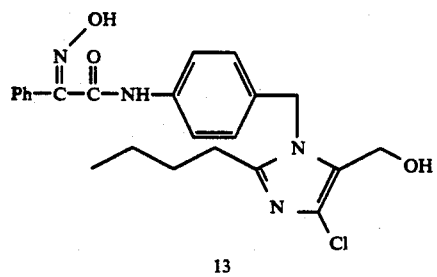

-continued
Scheme II

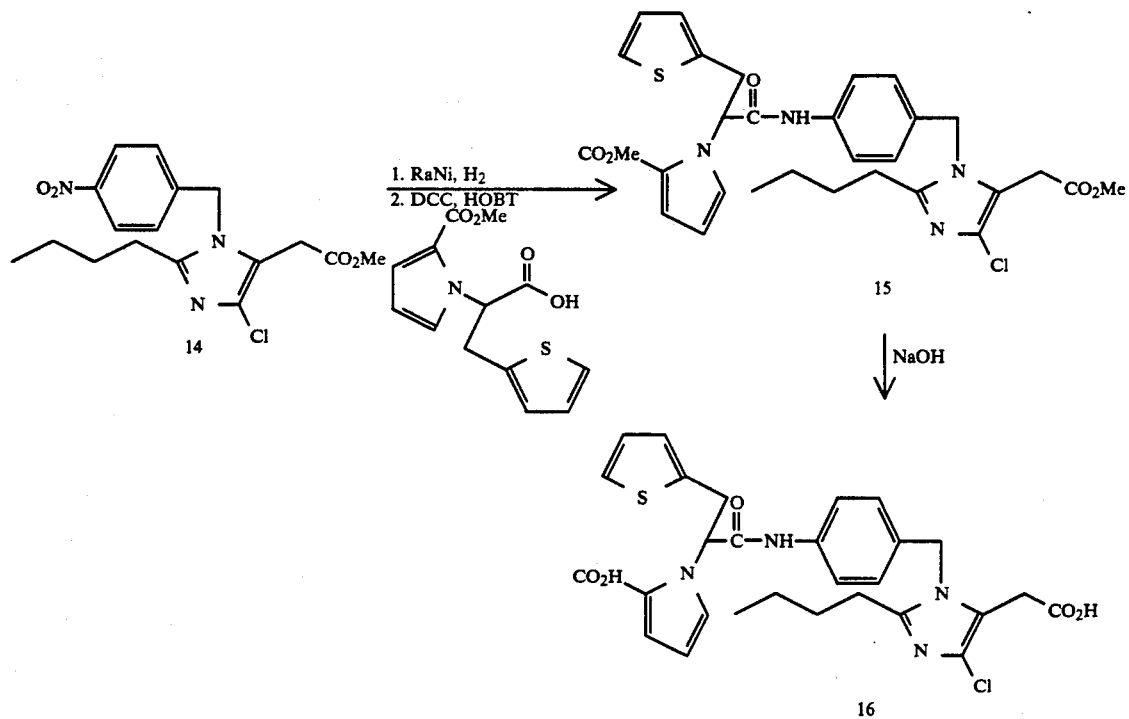

The effectiveness of the compounds of the instant invention is determined by a test (RBAT) entitled Receptor Binding of Angiotensin II. In this in vitro test the inhibition of tritiated angiotensin II binding to rat liver membranes is measured.

TABLE II

| Example | RBAT (µM) |
|---------|-----------|
| 8 | 0.21 |
| 8A | 1.56 |
| 8B | 8.37 |
| 8C | 1.58 |
| 8E | 8.8 |
| 8F | 2.9 |
| 8G | 1.3 |
| 8H | 11.1 |
| 9 | 2.45 |
| 9A | 2.19 |
| 9B | 3.66 |
| 9C | >10 |
| 9D | 1.28 |
| 10 | 0.82 |
| 10A | 0.20 |
| 10B | 0.14 |
| 10C | 0.60 |
| 10D | 0.29 |

TABLE II-continued

| Example | RBAT (µM) |
|---------|-----------|
| 10E | 1.48 |

Based on the observations that ACE inhibitors are known to benefit patients with heart failure, the instant compound which also interrupts the renin angiotensin system (RAS), would show similar benefits.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents. It can also be encapsulating material. In powders, the carrier is a finely divided solid which is in admixture with the finely divided active compound. In the tablet the active compound is mixed with a carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquified form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 0.1 to 1500 mg/kg of body weight per day or preferably 1 to 500 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

1-[(4-Aminophenyl)methyl]-2-butyl-4-chloro-1H-imidazole-5-methanol

Part 1

2-Butyl-4-chloro-1-[(4-nitrophenyl)methyl]-1H-imidazole-5-methanol

This compound was prepared in a manner analogous to that of Furakawa, et al, U.S. Pat. No. 4,355,040, Example 17. MP 91°–93° C. MS (EI) 324 (m+1).

Part 2

1-[(4-Aminophenyl)methyl]-2-butyl-4-chloro-1H-imidazole-5-methanol

A solution of the product from Part 1 (3.9 g) in THF (100 mL) was treated with Raney nickel (1.5 g) and hydrogenated at 50 psi for 3.5 hours. Catalyst was removed by filtration and the filtrate was evaporated. The resulting crystalline mass was triturated with isopropyl ether to give the title compound (3.2 g). MP 101°–103° C. MS (EI) 293 (m).

EXAMPLE 2

1-[(4-Aminophenyl)methyl]-5(propvlthio)-1H-1,3,4-triazole-2-methanol

Part 1

4-(Nitrophenyl)methyl]-carbamothioic acid, (hydroxyacetyl)hydrazide 4-nitrobenzylamine.HCl (3.8 g) was partitioned between $CH_2Cl_2$ (75 mL) and 0.5 N NaOH (50 mL). The organic layer was dried over $MgSO_4$ and filtered. The filtrate was treated with di-2-pyridylthiocarbonate (4.64 g), (*Tet. Lett.* 26, 1661 (1985)) and stirred at room temperature for 45 minutes. The resulting solution was treated with a solution of glycolic acid hydrazide (1.8 g) in methanol (25 mL) and the reaction was stirred overnight. The resulting suspension was filtered to afford the title hydrazide (5.2 g). MP 202°-204° C. MS (EI) 284 (m).

Part 2

5-Mercapto-4-[(4-nitrophenylmethyl]-4H-1,2,4-triazol-3-methanol

The product from Part 1 (5.0 g) was dissolved in 2 N NaOH (35 mL) and heated on a steam bath until the pot temperature reached 80° C. The resulting solution was then cooled on an ice bath while adding 2 N HCl (36 mL). The resulting yellow solid was collected by filtration and dried to afford the desired triazole (4.5 g). MP 219°-221° C. MS (EI) 266 (m).

Part 3

1-[(4 Nitrophenyl)methyl]-5-(propylthio)-1H-1,3,4-triazole-2-methanol

The product from Part 2 (1.1 g) was dissolved in DMF (20 mL) and treated with diisopropylamine (0.8 mL) and iodopropane (0.4 mL). The reaction was stirred overnight at room temperature and then evaporated. The residue was partitioned between EtOAc and water and the organic layer was washed with 0.1 N HCl, dried over MgSO$_4$, and evaporated to a solid which was triturated with ether to give the desired triazole (1.1 g). MS (EI) 308 (m).

Part 4

1-[(4-Aminophenyl)methyl]-5-(1-propylthio)-1H-1,3,4-triazole-2-methanol

The product from Part 3 (1.0 g) was dissolved in MeOH (100 mL) and treated with Raney nickel (0.2 g). The resulting suspension was hydrogenated at 50 psi for 16 hours and then filtered. The filtrate was evaporated to a solid (1.0 g) that was consistent with the title compound by $^1$H-NMR: $\delta$(CDCl$_3$) 7.0(d,2H), 6.6(d,2H), 5.5(br,1H), 5.1(s,2H), 4.7(s,2H), 3.8(br,2H), 3.1(t,2H), 1.7(m,4H), 1.0(t,3H).

EXAMPLE 3

Methyl 2 butyl-5-chloro-3 [(4-aminophenyl)methyl]-3H-imidazole-4-acetate

Part 1

SOCl$_2$ (37.9 mL, 0.52 mol) was added to a stirred solution of the hydroxy compound from Example 1, Part 1 (83.6 g, 0.26 mol) in CHCl3 (800 mL) at 10°-15° C. (ice-H$_2$O bath) over ½ hour. The resulting solution was stirred at 23° C. for 2½0 hours and then concentrated to dryness. The residual gum was taken up in CHCl$_3$(200 mL) and toluene (100 mL), and again concentrated to dryness to give the chloro compound. The residual semi-solid was dissolved in CHCl$_3$ (800 mL) and treated with a solution of NaCN (71.1 g, 1.45 mol), nBu4Br (9.7 g, 0.03 mol), and H$_2$O (400 mL) in a stream over 15 minutes. The resulting 2-phase mixture was stirred vigorously at room temperature for 2 hours. The layers were separated and the aqueous layer was extracted with CH$_2$Cl$_2$(300 mL). The combined organic layers were washed with H$_2$O (300 mL), dried (MgSO$_4$) and concentrated to dryness. The residual solid was recrystallized form CH$_2$Cl$_2$/ether (1/4,400 mL). Drying at room temperature for 18 hours afforded 72.5 g (84%) of the desired nitrile, MP, 121°-125° C.

Anal. calculated for C$_{16}$H$_{15}$ClN$_4$O$_2$(330.78): C,58.10; H,4.57; N,16.94; Cl,10.72.

Found: C,57.75; H,5.17; N,16.64; Cl,10.86.

MS (EI) 331 (m).

Part 2

A mixture of the above nitrile from Example 3, Part 1 (72 g, 0.218 mol) and 6N HCl (1 L) was heated under reflux for 3 hours. The solution was cooled to 0° C. and adjusted to pH 1 with the addition of 50% NaOH with stirring. After 30 minutes the solid was filtered off, rinsed with water and pressed as dry as possible under suction. The solid was dissolved in methanol (80 mL), iso-propanolol (400 mL) was added and the suspension was stirred at 0° C. for 2 hours. It was filtered, the residue was washed with iso-propanol and pressed dry under suction. The solid was finally dried under vacuum at 50° C. for 6 hours to afford 69 g of the desired acid, MP, 212°-213° C.

Anal. calculated for C$_{16}$H$_{18}$ClN$_3$O$_4$(351.79): C,54.63; H,5.16; Cl,10.08; N,11.94.

Found: C,54.72; H,5.16; Cl,10.18; N,11.90.

MS (FAB) 352 (m).

Part 3

HCl g was bubbled to a stirred mixture of the above acid (68.5 g) and CH$_3$OH (3.6 L) containing (MeO)$_3$CH (180 mL) for 30 minutes. The solution was gently heated at reflux for 2.5 hours and concentrated under vacuum to dryness. The gummy residue was triturated with EtOAc and the solid was filtered off. It was washed successively with EtOAc and ether and dried under suction for 12 hours. It was dissolved in hot EtOAc, filtered, and the filtrate concentrated to ca. 200 mL. Ether(300 mL) was added and the solution was allowed to stand at 0° C. for 3 hours to complete crystallization. The solid was filtered, washed with cold EtOAc followed by ether and dried under suction. It was finally dried under vacuum at 60° C. for 3 hours to afford 62 g of the title compound, MP; 101°-103° C.

Anal. calculated for C$_{17}$H$_{20}$OClN$_3$N$_4$: C,55.82; H,5.51; N,11.49; Cl,9.69.

Found: C,55.86; H,5.52; N,11.48; Cl,9.78.

MS: (EI) 366 (m).

Part 4

A solution of the product from Part 3 (4.97 g) in THF (100 mL) was treated with Raney Nickel (1.0 g) and hydrogenated at 50 psi for 4 hours. The catalyst was removed by filtration and the filtrate evaporated to give a white solid (4.5 g).

MS (EI) 335 (m).

This was used as is for condensation.

EXAMPLE 4

Part 1

Methyl 2-butyl-5-chloro-3-[(4-nitrophenyl)methyl]-3H-imidazole 4-propanoate

To a slurry of NaH (0.33 g, 8.5 mmol) in DMF (35 mL) was added diethyl malonate (1.12 g, 8.5 mmol) with stirring at 0° C. under nitrogen. The reaction mixture was stirred at room temperature for 40 minutes. A solution of the chloride (2.5 g, 7.7 mmol, prepared by the procedure described in Part 1, Example 3) in DMF (20 mL) was added dropwise with stirring and the reaction mixture was stirred for 18 hours. DMF was distilled under vacuum, the residue was taken up in $CH_2Cl_2$ and the solution was washed with water. It was dried over $MgSO_4$, evaporated and chromatographed (Hexane/$CH_2Cl_2$ ½-$CH_2Cl_2$—$CH_2Cl_2$/$CH_3OH$ 10%) to give 1.5 g of the desired product. MS (EI) 438 (m).

A solution of the above ester (1.0 g) in 6N HCl (15 mL) was heated at reflux for 4 hours. The solution was cooled and extracted with ether. The aqueous solution was adjusted to pH 3 and extracted with EtOAc. The extract was dried over $MgSO_4$ and evaporated to give 0.7 g of a foam. MS (EI) 365 (m).

Anal. calculated for $C_{17}H_{20}ClN_3O_4$: C,55.82; H,5.51; N,11.49.

Found: C,55.21; H,5.42; N,11.85.

A solution of the above acid in methanol (25 mL) and $H_2SO_4$ (0.5 mL) was heated at reflux for 2 hours. Usual workup gave 0.68 g of the title methyl ester. MS (EI) 380 (m). This was used as is for the next step.

Part 2

Methyl 3-[(4-aminophenyl)methyl]-2 butyl 5-chloro-3H-imidazole-4-propanoate

A solution of the above ester (2.15 g) in THF (100 mL) was hydrogenated at 50 psi in presence of Raney nickel. Usual workup gave the crude product (2.0 g) which was chromatographed to yield 1.52 g of the pure title amino compound. MS (EI) 350 (m).

EXAMPLE 5

Part 1

2-Butyl 4-methyl-1-[(4-nitrophenyl)methyl]-1H-benzimidazole

To a slurry of NaH (60%, 0.21 g. 5.3 mmol) in DMF was added with stirring a solution of 2-butyl-4-methyl-benzimidazole (1 g. 5.3 mmol) in DMF (20 mL under nitrogen atmosphere. After the gas evolution was complete, the reaction mixture was cooled in ice and a solution of 4-nitrobenzyl bromide (1.5 g, 5.3 mmol) in DMF (5 mL) was added with stirring. The reaction mixture was allowed to warm up slowly to room temperature and stirred for 16 hours. DMF was distilled under reduced pressure and the residue was taken up in EtOAc, and the solution was washed with water. It was dried over $MgSO_4$ and evaporated to give a solid which was chromatographed ($CH_2Cl_2$/EtOAc 4/1-EtOAc) to give 1.5 g of a solid, MP 115°–116° C.

Anal. calculated for $C_{19}H_{21}N_3O_2$: C,70.57; H,6.55; N,12.99.

Found: C,70.46; H,6.64; N,12.94.

MS (EI) 323 (m).

Part 2

4-[2-Butyl-4-methyl-1H-benzimidazol-1-yl)methyl]-benzeneamine

A solution of the above nitro compound (1.5 g) in a mixture of THF/EtOH (50/200 mL) was hydrogenated at 50 psi in presence of Raney nickel (1 g). The catalyst was filtered and the filtrate was evaporated to give a white residue (1.4 g).

Anal. calculated for $C_{19}H_{23}N_3$: C,77.78; H,7.90; N,14.32.

Found C,77.32; H,7.90; N,14.02.

MS (EI) 293 (m).

The following compounds were prepared by replacing the benzimidazole derivative in the above b]pyridine.

EXAMPLE 6

Part 1

5,7 Dimethyl-2-ethyl-3-[(4-nitrophenyl)methyl]-3H-imidazo[4,5-b]pyridine

MS (CI) 311 (m+1);

Anal. calculated for $C_{17}H_{18}N_4O_2$: C,65.79; H,5.85; N,18.05.

Found: C,65.26; H,5.94; N,17.99

Part 2

4-[(5,7-Dimethyl-2-ethyl-3H-imidazo[4,5 b]pyridine-3-yl)methyl]benzeneamine

MS (CI) 281 (m+1)

EXAMPLE 7

Preparation of the pyrrole carboxylic acids.

7A.

2-(Methoxycarbonyl)-α-(phenylmethyl)-1H-pyrrole-1-acetic acid

A mixture of L phenyl alanine (13 g, 79 mmol) and NaOAc (38.8 g, 470 mmol) in AcOH (250 mL) was heated to reflux for 30 minutes to give a clear solution. Methyl 2,5-dimethoxy tetrahydrofuran-2-carboxylate (15 g, 79 mmol) was added and the solution was refluxed for 4 minutes. The dark brown solution was poured into 1 L of ice-water and extracted with EtOAc (3×250 mL). The organic extract was washed with water, dried over anhydrous $MgSO_4$, and evaporated to a brown gum which was chromatographed to give 10 g of a viscous oil. Mass spectrum indicate correct mass ion (273) for the compound. $[\alpha]D^{23}$, 17.5° C. (c, 1.0 in MeOH).

Anal. calculated for $C_{15}H_{15}NO_4$:0.4 EtOAc: C,64.62; H,5.95; N,4.54.

Found: C,64.86; H,5.77; N,4.44.

The following analogs were prepared by replacing phenyl alanine with the requisite amino acids in the above procedure.

7B. 2-(Methoxycarbonyl)-α-(2-(DL) thienylmethyl)-1H-pyrrole-1-acetic acid

MS (EI) 279 (m). MP 115°–116° C.

Anal. calculated for $C_{13}H_{13}NO_4S$: C,55.90; H,4.69; N,5.01.

Found: C,55.63; H,4.70; N,4.89.

7C.

2-(Methoxycarbonyl)-α-phenyl-1H-pyrrole-1-acetic acid

MS (EI) 259 (m)

7D. 2-(Methoxycarbonyl)-1H -pyrrole-1-acetic acid

MS (EI) 183 (m)

7E. α-Butyl-2-(methoxycarbonyl)-1H-pyrrole-1-acetic acid

MS (EI) 239 (m)

7F.
3-(Ethoxycarbonyl)-2-methyl-α-(phenylmethyl)-1H-pyrrole 1 acetic acid The title compound was prepared by substituting ethyl 5-acetoxy-2-methyl-4,5-dihydrofuran-3-carboxylate (Cambie, R. C., Moratti, S. C., Rutledge, P. S., Woodgate, P. D; Synthetic Communication, 20(13), 1923-1929, 1990; in place of 2,5-dimethoxy-tetrahydrofuran derivate in Example 7A. MS (EI) 301 (m)

EXAMPLE 8

(S) 1H-Pyrrole-2-carboxylic acid, 1-[2-[[4-[[2-butyl-4-chloro-5-(hydroxymethyl)-1H-imidazol-1-yl]methyl]-phenyl]amino]-2-oxo-1-(phenylmethyl)ethyl]methyl ester A solution of 0.36 g (1.3 mmol) of the acid 7A, 0.17 g (1.3 mmol) of HOBT, and 0.38 g (1.3 mmol) of the aniline of Example 1 in 5 mL of DMF was cooled in ice and treated with 0.27 g (1.3 mmol) of DCC in 5 mL of DMF. After 0.5 hours at 0° C., the mixture was allowed to stir at room temperature for 48 hours. The urea was filtered off and the residue was washed with $CH_2Cl_2$. The filtrate and the washings were combined and filtered to remove additional quantity of urea, and stripped under vacuum. The residue was diluted with EtOAc and the ethyl acetate layer was washed successively with water, saturated $NaHCO_3$, and brine. Drying and removal of the solvent under reduced pressure gave the crude product. This was purified via chromatography ($SiO_2$, $CH_2Cl_2/CH_3OH$, 5%) to give 0.4 g of product. The structure was confirmed by mass spectroscopy (molecular ion mass: and NMR. MP 180°-185° C.

Anal. calculated for $C_{36}H_{33}N_4O_4Cl.0.25$ $CH_2Cl_2$: C,63.71; H,5.88; N,9.88.

Found: C,63.49; H,6.02; N,9.80.

The following additional compounds were prepared by the procedure described in Example 8.

8A. (S) 1H-Pyrrole-2-carboxylic acid, 1-[2-[[4-[2-butyl-4-chloro-5-(hydroxymethyl)-1H-imidazol-1-yl]methyl]phenyl]amino]-2-oxo-1-(phenyl)ethyl]methyl ester MS [FAB], 535 (m)

8B. (S) 1H-Pyrrole-2-carboxylic acid, 1-[2-[4-[[2-butyl-4-chloro 5-(hydroxymethyl) 1H-imidazol-1-yl]methyl]phenyl]amino]-2-oxoethyl]-methyl ester Mass spectrum indicate correct mass ion (459) for the compound.

Anal. calculated for $C_{23}H_{27}ClN_4O_4$: C,60.21; H,5.88; N,12.20.

Found: C,60.01; H,6.24; N,11.90.

8C. (S) 1H-Pyrrole 2-carboxylic acid, 1-[2 [-4-[2-butyl-4-chloro-5-(hydroxymethyl) 1H imidazol 1-yl]methyl]phenyl]amino] 1 butyl-2-oxoethyl]-methyl ester Mass spectrum indicate correct mass ion (515) for the compound.

Anal calculated for $C_{27}H_{35}ClN_4O_4$: C,62.96; H,6.85; N,10.88.

Found: C,62.87; H,6.89; N,10.71.

8D. (S) 1H-Pyrrole-2 carboxylic acid, 1-[2-[[4-[[3-(hydroxymethyl) 5-(propylthio)-4H-1,2,4-triazol-4-yl]methyl]phenyl]amino]-2-oxo-1-(phenylmethyl)ethyl]methyl ester By replacing the aniline of the Example 1 with the aniline of Example 2, and by following the procedure discussed in Example 8, the title compound is obtained. MS (EI) 533 (m).

8E. (S) N-4-[2-Butyl-4-chloro-5-(hydroxymethyl)-1H-imidazole-1-yl]methyl]phenyl]-α-oxo-benzeneacetamide By replacing the pyrrole acetic acid in Example 8 with benzoylformic acid, 0.45 g of the title compound was obtained. The structure was confirmed by mass spectroscopy (molecular ion, 425) and microanalysis.

Anal. calculated for $C_{23}H_{24}ClN_3O_3.0.32$ $H_2O$ C,64.00; H,5.75; N,9.73.

Found: C,64.05; H,5.71; N,9.64.

8F. N [4-[[2-Butyl-4-chloro-5-(hydroxymethyl)-1H-imidazol-1-yl]methyl]phenyl]-α-cyano-benzenepropanamide By replacing the pyrroleacetic acid in Example 8 with 2 cyano-3-phenylpropionic acid, the title compound was obtained. The structure was confirmed by mass spectroscopy (molecular ion, 450).

8G. N 4-[[2 Butyl 4 chloro-5-(hydroxymethyl)-1H-imidazol-1-yl]methyl]-phenyl]-α-(hydroxyimino)benzeneacetamide A solution of 0.35 g of the compound from Example 8E was dissolved in 10 mL of EtOH and treated with a solution of $NH_2OH.HCl$ (0.1 g) and NaOAc (0.15 g) in water (2 mL). The mixture was heated to reflux for 18 hours. The solution was evaporated to dryness and the residue was taken up in EtOAc. The EtOAc extract was washed with water, dried, and stripped to yield a foam which was triturated with $Et_2O$ and filtered to give 0.31 g of a white solid. Mass spectrum indicates molecular ion (441) of the desired oxime.

Anal. for $C_{23}H_{25}ClN_4O_3.0.5$ $CH_3CO_2H.0.5$ EtOH: C,60.79; H,6.07; N,11.34.

Found: C,60.82; H,5.87; N,11.27.

8H. N [4-[[2 Butyl-4-chloro-5-(hydroxymethyl)-1H-imidazol-1-yl]methyl]phenyl]-α-(phenylmethyl)-1H tetrazole-5-acetamide A mixture of 8F (0.5 g, 1.11 mmol), $NaN_3$ (0.19 g, 2.9 mmol) and $NH_4Cl$ (0.06 g, 1.12 mmol) in DMF (5 mL) was heated at 80° C. for 18 hours. DMF was distilled under vacuum and the residue was partitioned between water and EtOAc. The aqueous solution was acidified with concentrated HCl and extracted with $CH_2Cl_2$. The organic layer was separated, washed with water, dried over $MgSO_4$ and evaporated to yield 0.15 g of the title compound as a white foam. MS (FAB) 494 (m).

EXAMPLE 9

(RS) Methyl 2-butyl-5-chloro 3-[[4-[[2-[2-(methoxycarbonyl)-1H-pyrrol-1-yl]-1-oxo-3-(2-thienyl)propyl]-amino]phenyl]methyl]-3H-imidazole 4 acetate DMAP (1.5 g, 12.32 mol) was added to an ice cold solution of the acid (1.56 g, 5.6 mmol, of Example 7B) in THF (20 mL). A solution of t-butyl acetylchloride (0.76 mL, 6.16 mol) in THF (10 mL) was added dropwise with stirring. The reaction mixture was stirred for 2 hours at 0° C. followed by the addition of a THF (15 mL) solution of 1.85 g (5.6 mmol) the aniline of Example 3. The reaction mixture was allowed to warm up to room temperature and stirred for 18 hours. It was filtered and the residue was washed with THF. The filtrate and the washings were combined and evaporated. The residue was taken up in EtOAc and the solution was washed with water, dried over anhydrous MgSO$_4$, and evaporated to yield a gum. It was chromatographed [CH$_2$Cl$_2$/EtOAc (9:1) - EtOAc] to give the title compound as a solid, MP. 171°–172° C. Mass spectrum indicate correct mass ion (597) for the compound.

Anal. calculated for C$_{30}$H$_{33}$ClN$_4$O$_5$S, 0.3 CH$_2$Cl$_2$ (622.618): C,58.45; H,5.44; N,9.00.

Found: C,58.49; H,5.49; N,9.00.

(S) Methyl 2-butyl-5-chloro-3-[[4-[[2-[2-(methoxycarbonyl)-1H-pyrrol-1-yl]-1-oxo-3-(2-thienyl)propyl]-amino]phenyl]methyl]-3H-imidazole-4-acetate is similarly prepared.

Ms (FAB) 597 (m)

The following additional compounds were prepared by the procedure described in the Example above.

9A. (S) Methyl 2 butyl-5-chloro 3-[[4-[[2-[2-(methoxycarbonyl)-1H-pyrrol-1-yl]-1 oxo-3-phenyl]methyl-3H-imidazole phenylpropyl]amino 4-acetate MP. 186°–188° C. Mass spectrum indicate correct mass ion (591) for the compound.

Anal. calculated for C$_{32}$H$_{35}$ClN$_4$O$_5$: C,65.02; H,5.97; N,9.48.

Found: C,64.88; H,6.13; N,9.27.

9B. (S) Methyl 2-butyl-5-chloro 3-[[4-[[2-[[3-(ethoxycarbonyl)-2-methyl]-1H pyrrol 1-yl]-1-oxo-3-phenylpropyl]amino]phenyl]methyl]-3H-imidazole-4-acetate Mass spectrum indicate correct mass ion (619) for the compound.

Anal. calculated for C$_{34}$H$_{39}$ClN$_4$O$_5$: C,65.96; H,6.35; N,9.04.

Found: C,65.87; H,6.41; N,9.36.

9C. (S) Methyl 1-[2-[[4-[(2-butyl-4-methyl-1H-benzimidazol-1-yl)methyl]phenyl]amino]-2-oxo-1-(phenylmethyl)ethyl]-1H-pyrrole-2-carboxylate

MP. 202°–203° C.

Anal. calculated for C$_{34}$H$_{36}$H$_4$O$_3$, 0.5 CH$_3$OH: C,73.38; H,6.78; N,9.92.

Found: C,73.05; H,6.48; N,10.24.

Mass spectrum indicate correct mass ion (549) for the compound.

9D. (S) Methyl 2-butyl-5-chloro-3-[4-[2-[2-(methoxycarbonyl)-1H-pyrrol-1-yl]-1-oxo-3-phenylpropyl]amino[phenyl]-methyl]-3H-imidazole-4-propanoate Mass spectrum indicate correct molecular ion (605) for the compound.

Anal. calculated for C$_{33}$H$_{37}$ClN$_4$O$_5$: C,65.50; H,6.16; N,9.26.

Found: C,65.28; H,6.10; N,9.15.

9E. (S) Methyl 1-[2-[4-[5,7-dimethyl-2-ethyl-3H-imidazol4,5-b]pyridin-3-yl)methyl]phenyl]-amino]2 oxo-1-(phenylmethyl)ethyl]-1-pyrrole-2-carboxylate MS (EI) 536 (m)

EXAMPLE 10

(S) 1H-Pyrrole-2-carboxylic acid, 1-[2-[[4-[2-butyl-4-chloro-5-(hydroxymethyl)-1H-imidazol-1-yl]methyl-phenyl]amino]-2-oxo-1-(phenylmethyl)ethyl]]

A mixture of 0.2 g of the compound of Example 8 and 30 mg of NaOH in a mixture of THF/H$_2$O (205 mL) was stirred overnight at room temperature. THF was distilled off, the residue was treated with water, and the solution was extracted with EtOAc. The aqueous solution was adjusted to pH 5 and extracted with EtOAc. The EtOAc extract was washed with water, dried, stripped to give a yellow foam, and chromatographed (CH$_2$Cl$_2$/CH$_3$OH 10%) to give 0.1 g of the title compound as a white solid.

Anal. calculated for C$_{29}$H$_{31}$ClN$_4$O$_4$; 0.1 CH$_2$Cl$_2$: C,64.31; H,5.79; N,10.31.

Found: C,64.13; H,5.96; N,10.35.

MS (FAB) 535 (m).

The following compounds were prepared by the procedure described in the Example 10.

10A. (S) 2-Butyl 3-[[4-[[2-(2-carboxy-1H-pyrrol 1 yl)-1-oxo-3-phenylpropyl]amino]phenyl]methyl]-5-chloro-3H-imidazole-4-acetic acid Anal. calculated for C$_{30}$H$_{31}$ClN$_4$O$_5$. 0.53 AcOH: C,62.71; H,5.61; N,9.42.

Found: C,62.79; H,5.26; N,9.17.

Mass spectrum indicate correct mass ion (563) for the compound.

10B. (S) 2-Butyle-3-[[4-[[2-(2-carboxy-1H-pyrrol-1yl) 1-oxo-3-(2-thienyl)propyl]amino]phenyl]methyl]-5-chloro-3H-imidazole-4-acetic acid Anal. calculated for C$_{28}$H$_{29}$ClN$_4$O$_5$S. 0.5 H$_2$O: C,58.12; H,5.24; N,9.68.

Found: C,58.12; H,5.13; N,9.72.

Mass spectrum indicate correct mass ion (569) for the compound. MP. 192°–193° C.

10C. (S) 2-Butyl-3-[[4-[2-(3-ethoxycarbonyl-2-methyl-1H-pyrrol-1-yl)-1-oxo-3-phenylpropyl]amino]phenyl]methyl]-5-chloro-3H-imidazole-4-acetic acid Mass spectrum indicate correct mass ion (605) for the compound.

10D. (S)
2-Butyl-5-chloro-3-[[4-[[2-[2-(methoxycarbonyl)-1H-pyrrol-1-yl]-1 oxo-3-phenylpropyl]amino]phenyl]methyl]3H-imidazole 4-propanoic acid Anal. calculated for $C_{31}H_{33}ClN_4O_5$: C,64.52; H,5.76; N,9.71.
Found: C,64.89; H,5.87; N,9.45.
Mass spectrum indicate correct mass ion (577) for the compound.

10E. (S)
1-[2-[[4-[(2-Butyl-4-methyl-1H-benzimidazol-1-yl)methyl]phenyl]amino]-2-oxo-1-(phenylmethyl)ethyl]-1H-pyrrole-2-carboxylic acid Mass spectrum indicate correct mass ion (535) for the compound. cl 10F. (S) 1-[2-[[4-[(5,7-Dimethyl-2-ethyl-3H-imidazo[4,5-pyridin-3-yl)methyl -phenyl]amino-2-oxo 1-(phenylmethyl)ethyl]-1H-pyrrole-2-carboxylic acid MS (FAB) 522 (m)

10G. (S)
2Butyl-3-[[4-[[2-(3-carboxy-2-methyl-1H-pyrrol-1-yl) -1-oxo-3-phenylpropyl]amino]phenyl]methyl]-5-chloro-3H-imidazole-4-acetic acid MS (FAB) 577 (m)

10H. (S) Methyl
2-butyl-4-chloro-1-[[4-[[2-[2-(methoxycarbonyl) -1H-pyrrol-1-yl]-1 oxo-3-phenylpropyl]amino]phenyl]methyl]-1H-imidazole-5-carboxylate MS (FAB) 577 (m)

10I. (S) 2-Butyl-1-[4-[[2-(2-carboxy-1H pyrrol-1-yl) -1-oxo-3-phenylpropyl]amino]phenyl]methyl]-4-chloro-1H-imidazole-5-carboxylic acid MS (FAB) 549 (m)

I claim:
1. A compound of formula

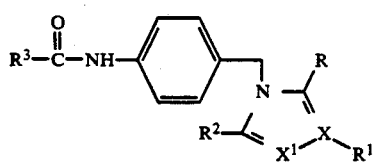

or the pharmaceutically acceptable acid addition or base salts thereof, wherein:
X and $X^1$ are each independently carbon or nitrogen and only one is nitrogen;
R and $R^1$ are each independently
hydrogen,
halogen,
lower alkyl,
alkyl carboxylate,
alkyl carboxylic acid,
trihalomethyl,
perfluoroethyl,
$CH_2CO_2CH_3$,
$CH_2COC_2H_5$,
cyano,
cyanomethyl,
$CH_2CONH_2$,
$CH_2CONHCH_3$,
$CH_2CON(CH_3)_2$,
alkoxymethyl,
hydroxymethyl,
alkylthiomethyl,
thiomethyl,
COOH,
$CO_2$alkyl,
$(CH=CH)CO_2R_8$,
—$(CH_2)_n CO_2R_8$ wherein
$R_8$ is H or lower alkyl,
—$(CH_2)_n C \equiv N$,
CHO,
1-oxoalkyl,
2-oxoalkyl, or
3-oxoalkyl
with the proviso that when X is nitrogen, $R^1$ is absent, when X is carbon, R and $R^1$ each independently vinyl; cycloalkylidenyl with from 5 to 6 members in the ring; alkynyl of 2 to 10 carbon atoms; phenylalkynyl where the alkynyl portion is 2 to 6 carbon atoms, aryl;
$R^2$
propyl,
butyl,
cycloalkyl
—$CH_2CH'CH_2$,
—$CH=CHCH_3$,
—$CH_2CH=CH—CH_3$,
—$CH=CHCH_2CH_3$,
—$CH_2CH_2CH=CH_2$,
—$CH_2C\equiv CH$,
—$C\equiv C—CH_3$,
—$C\equiv C—CH_2CH_3$,
—$CH_2C\equiv CCH_3$,
—$CH_2CH_2C\equiv CH$,
—$SCH_3$,
—$SC_2H_5$,
—$SC_3H_7$,
—$SC_4H_9$,
—$OCH_3$,
—$OC_2H_5$,
—$OC_3H_7$,
—$OC_4H_9$,
—$SCH_2CH=CH_2$,
—$OCH_2CH=CH_2$,
$SCH_2C\equiv CH$, or
—$OCH_2C\equiv CH$; and
$R_3$ is

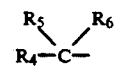

wherein $R_4$ is hydrogen, lower alkyl, aryl, unsubstituted or substituted with halo, alkyl, alkyloxy, hydroxy, arylalkyl, unsubstituted or substituted with halo, alkyl, alkyloxy, hydroxy, heteroaryl, unsubstituted or substituted with halo, alkyl, alkyloxy, hydroxy, or heteroarylalkyl, unsubstituted or substittued with halo, alkyl, alkyloxy, hydroxy wherein heteroaryl is selected from: pyrrole, imidazole, thiophene, furan, pyridine, thiazole, indole, morpholine, isoquinoline;
$R_5$ is hydrogen, and
$R_6$ is —$C\equiv N$, —COOH, tetrazole, or

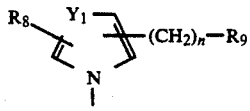

wherein $Y_1$ is CH or N, n is from 0 to 2, $R_9$ is H, lower alkyl, aryl, —CN, —$COR_8$, —$CO_2R_8$,

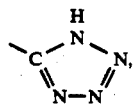

wherein $R_8$ is hydrogen or lower alkyl; when $Y_1$ is CH, $Y_1$ and $R_8$ may together form

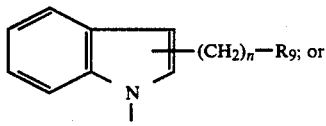

$R_5$ and $R_6$ together are

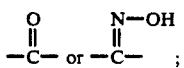

alkyl is a carbon group of from 1 to 3 atoms and aryl is phenyl or naphthyl.

2. A compound according to claim 1 wherein
X and $X^1$ are each independently carbon or nitrogen;
R and $R^1$ are each independently,
—$CH_2OH$,
—$CH_2SH$,
—$CH_2OCH_3$,
—$CH_2SCH_3$,
—CHO,

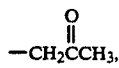

—$CF_3$,
—$CH_2CF_3$,
—$CH_3$,
—H,
—Cl,
—Br,
—F,
[CH=CHCHCO$_2$R$_8$]
—CH=CHCHCO$_2$R$_8$,
—(CH$_2$)$_n$CO$_2$R$_8$, wherein R$_8$ is H or lower alkyl;
—(CH$_2$)$_n$C≡N,
—(CH$_2$)$_n$CONH$_2$,
—(CH$_2$)$_n$CONHCH$_3$, or
—(CH$_2$)$_2$CON(CH$_3$)$_2$ wherein n is 0, 1, or 2;
with the proviso that when X is nitrogen, $R^1$ is absent;
$R^2$ is
propyl,
butyl,
cyclopropyl,
thiomethyl,
thioethyl,
thiopropyl,
thiobutyl,
—CH$_2$CH=CH$_2$,
—CH$_2$CH=CH—CH$_3$,
—CH$_2$CH$_2$CH=CH$_2$,
—CH$_2$C≡CCH$_3$,
—CH$_2$CH$_2$C≡CH,
—OCH$_3$,
—OCH$_2$H$_5$,
—OC$_3$H$_7$,
—OC$_4$H$_9$,
—SCH$_2$CH=CH$_2$ or
—OCH$_2$CH=CH$_2$; and
$R_3$ is as defined in claim 1.

3. A compound according to claim 1 wherein
X is carbon;
$X^1$ is nitrogen;
R is
—CH$_2$OH;
—CH$_2$OCH$_3$,
—(CH$_2$)$_n$CO$_2$R$_8$, or
—Cl;
$R_1$ is
—H,
—CH$_2$OH,
—CH$_2$OCH$_3$,
—CH$_2$CO$_2$CH$_3$,
—Cl,
—Br,
—CF$_3$ or
—CF$_2$CH$_3$;
$R_2$ is
—C$_4$H$_9$;
—C$_3$H$_7$,
—SC$_2$H$_5$, or
—SC$_3$H$_7$; and
$R_3$ is

wherein n, $R_4$ and $R_9$ are as defined in claim 1.

4. A compound according to claim 1 wherein
R is (CH$_2$)$_n$CO$_2$H wherein n is an integer of from 0 to 2;
X is carbon,
$X^1$ is nitrogen,
$R^1$ is Cl or Br,
$R^2$ is butyl or propyl,
$R^3$ is

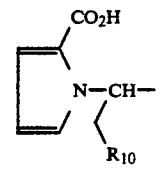

wherein $R_{10}$ is phenyl or thienyl.

5. A pharmaceutical composition for treating hypertension associated with the renin antiotensin system in mammals comprising an antihypertensive amount of a compound according to claim 1 togehter with a pharamecutically acceptable carrier.

6. A method for treating hypertension in a mammal suffering therefrom comprising administering to said mammel in an antihypertensive effective amount of a composition according to claim 5.

7. A compound selected from the list consisting of:

(S)1H-pyrrole-2-carboxylic acid, 1-[2-[[4-[[2-butyl-4-chloro-5-(hydroxymethyl) -1H-imidazol-1-yl]methyl]phenyl]amino]-2-oxo-1-(phenylmethyl)ethyl]-methyl ester;

(S)1H-pyrrole-2-carboxylic acid, 1-[2-[[4-[[2-butyl-4-chloro-5-(hydroxymethyl) -1H-imidazol-1-yl]methyl]phenyl]amino]-2-oxo-1-(phenylmethyl)ethyl];

N-[4-[[2-butyl-4-chloro-5-(hydroxymethyl)-1H-imidazol-1-yl]methyl]phenyl]-α-oxo-benzeneacetamide;

N-[4-[[2-butyl-4-chloro-5-(hydroxymethyl)-1H-imidazol-1-yl]methyl]phenyl]-α-(hydroxyimino)benzeneacetamide;

N-[4-[[2-butyl-4-chloro-5-(hydroxymethyl)-1H-imidazol-1-yl]methyl]phenyl]-α-cyano-benzenepropanamide;

(S)1H-pyrrole-2-carboxylic acid, 1-[2-[[4-[[2-butyl-4-chloro-5-(hydroxymethyl) -1H-imidazol-1-yl]methyl]phenyl]amino]-2-oxo-1-phenylethyl] methyl ester;

(S)1H-pyrrole-2-carboxylic acid, 1-[2-[[4-[[2-butyl-4-chloro-5-(hydroxymethyl) -1H-imidazol-1-yl]methyl]phenyl]amino]-1-butyl-2-oxoethyl] methyl ester;

(S)1H-pyrrole-2-carboxylic acid, 1-[2-[[4-[[2-butyl-4-chloro-5-(hydroxymethyl) -1H-imidazol-1-yl]methyl]phenyl]amino]-2-oxoethyl] methyl ester;

(S) Methyl 2-butyl-5-chloro-3-[[4-[[2-[2-(methoxycarbonyl) -1H-pyrrol-1-yl]-1-oxo-3-(2-thienyl)propyl]amino]phenyl]methyl]-3H-imidazole-4-acetate;

(S) Methyl 2-butyl-5-chloro-3-[[4-[[2-[2-(methoxycarbonyl) -1H-pyrrol-1-yl]-1-oxo-3-(2-thienyl)propyl]amino]phenyl]methyl]-3H-imidazole-4-acetate;

(S) Methyl 2-butyl-5-chloro-3-[[4-[[2-[3-(ethoxycarbonyl) -2-methyl]-1H-pyrrol-1-yl]-1-oxo-3-phenylpropyl]amino]phenyl]methyl]-3H-imidazole-4-acetate;

(S) Methyl 2-butyl-5-chloro-3-[[4-[[2-[2(methoxycarbonyl) -1H pyrrol-1-yl[-1-oxo-3-phenylpropyl]amino]phenyl]methyl]-3H-imidazole-4-propanoate;

(S) 1H-Pyrrole-2-carboxylic acid, 1-[2-[[4-[[2-butyl-4-chloro-5-(hydroxymethyl) -1H-imidazol-1-yl)methyl]phenyl]amino]-2-oxo-1-(phenylmethyl)ethyl];

(S) 2-Butyl-3-[[4-[[-2-(-2-carboxy-1H-pyrrol-1-yl)-1-oxo-3-phenylpropyl]amino]phenyl]methyl]-5-chloro-3H-imidazole-4-acetic acid;

(S) 2-Butyl-3-[[4-[[-2-(-2-carboxy-1H-pyrrol-1-yl)-1-oxo-3(2-thienyl) propyl]amino]phenyl]methyl]-5-chloro-3H-imidazole-4-acetic acid;

(S) 2-Butyl-3-[[4-[[2-(3-ethoxycarbonyl-2-methyl-1H-pyrrol-1-yl) -1-oxo-3-phenylpropyl]amino]phenyl]methyl]-5-chloro-3H-imidazole-4-acetic acid;

(S) 2-Butyl-5-chloro-3-[[4-[[2-[2-(methoxycarbonyl) -1H-pyrrol-1-yl]-1-oxo-3-phenylpropyl]amino]phenyl]methyl]3H-imidazole-4-propanoic acid;

(S) 2-Butyl-3-[[4-[[2-(3-carboxy-2-methyl-1H-pyrrol-1-yl) -1-oxo-3-phenylpropyl]amino]phenyl]methyl]-5-chloro-3H-imidazole-4-acetic acid;

(S) Methyl 2-Butyl-4-chloro-1-[[4-[[2-[2-(methoxycarbonyl)-1H-pyrrol-1-yl]-1-oxo-3-phenylpropyl]amino phenyl]methyl]-1H-imidazole-5-carboxylate; and (S) 2-Butyl-1-[[4-[[2-2-carboxy-1H-pyrrol-1yl)-1-oxo-3-phenylpropyl]amino]phenyl]methyl]-4-chloro-1H-imidazole-5-carboxylic acid;

or their pharmaceutically acceptable salts.

* * * * *